US008940340B2

(12) United States Patent
Weissman et al.

(10) Patent No.: US 8,940,340 B2
(45) Date of Patent: Jan. 27, 2015

(54) SYSTEMS AND METHODS FOR MAINTAINING THE DOMINANCE OF *NANNOCHLOROPSIS* IN AN ALGAE CULTIVATION SYSTEM

(75) Inventors: Joseph Weissman, Vero Beach, FL (US); Guido Radaelli, Oakland, CA (US)

(73) Assignee: Aurora Algae, Inc., Hayward, CA (US)

( * ) Notice: Subject to any disclaimer, the term of this patent is extended or adjusted under 35 U.S.C. 154(b) by 322 days.

(21) Appl. No.: 12/321,767

(22) Filed: Jan. 22, 2009

(65) Prior Publication Data
US 2010/0183744 A1    Jul. 22, 2010

(51) Int. Cl.
*A01N 59/08*    (2006.01)
*A61K 33/14*    (2006.01)
*A01N 65/00*    (2009.01)
*A61K 36/02*    (2006.01)
*C12N 1/12*    (2006.01)
*A01N 59/00*    (2006.01)
*C12P 7/64*    (2006.01)

(52) U.S. Cl.
CPC ....... *C12N 1/12* (2013.01); *A01N 59/00* (2013.01); *C12P 7/649* (2013.01); *Y02E 50/13* (2013.01)
USPC ............................. 424/665; 424/195.17

(58) Field of Classification Search
CPC ......... A01N 59/00; A01N 25/00; C12N 1/12; C12N 1/04; C12P 7/6463; C12P 7/649; Y02E 50/13
See application file for complete search history.

(56) References Cited

U.S. PATENT DOCUMENTS

| | | |
|---|---|---|
| 1,926,780 A | 9/1933 | Lippincott |
| 3,220,706 A | 11/1965 | Valdespino |
| 3,468,057 A | 9/1969 | Buisson |
| 3,897,000 A | 7/1975 | Mandt |
| 3,955,318 A | 5/1976 | Hulls |
| 4,003,337 A | 1/1977 | Moore |
| 4,115,949 A | 9/1978 | Avron et al. |
| 4,217,728 A | 8/1980 | Shimamatsu et al. |
| 4,267,038 A | 5/1981 | Thompson |
| 4,365,938 A | 12/1982 | Warinner |
| 4,535,060 A | 8/1985 | Comai |
| 4,658,757 A | 4/1987 | Cook |
| 4,813,611 A | 3/1989 | Fontana |
| 5,105,085 A | 4/1992 | McGuire et al. |
| 5,130,242 A | 7/1992 | Barclay |
| 5,227,360 A | 7/1993 | Sherba et al. |
| 5,338,673 A | 8/1994 | Thepenier et al. |
| 5,353,745 A | 10/1994 | Fahs, II |
| 5,478,208 A | 12/1995 | Kasai |
| 5,518,990 A | 5/1996 | Ushio et al. |
| 5,527,456 A | 6/1996 | Jensen |
| 5,539,133 A | 7/1996 | Kohn et al. |
| 5,564,630 A | 10/1996 | Giles et al. |
| 5,573,669 A | 11/1996 | Jensen |
| 5,658,076 A | 8/1997 | Crump et al. |
| 5,658,767 A | 8/1997 | Kyle |
| 5,823,781 A | 10/1998 | Hitchcock et al. |
| 5,871,952 A | 2/1999 | Ghirardi et al. |
| 6,000,551 A | 12/1999 | Kanel et al. |
| 6,117,313 A | 9/2000 | Goldman |
| 6,166,231 A | 12/2000 | Hoeksema |
| 6,192,833 B1 | 2/2001 | Brune et al. |
| 6,372,460 B1 | 4/2002 | Gladue et al. |
| 6,447,681 B1 | 9/2002 | Carlberg et al. |
| 6,524,486 B2 | 2/2003 | Borodyanski et al. |
| 6,579,714 B1 | 6/2003 | Hirabayashi et al. |
| 6,626,738 B1 | 9/2003 | Shank |
| 6,736,572 B2 | 5/2004 | Geraghty |
| 6,750,048 B2 | 6/2004 | Ruecker et al. |
| 6,831,040 B1 | 12/2004 | Unkefer et al. |
| 6,871,195 B2 | 3/2005 | Ryan et al. |
| 6,896,804 B2 | 5/2005 | Haerther et al. |
| 6,944,013 B2 | 9/2005 | Yang |
| 7,333,195 B2 | 2/2008 | Krei.beta. et al. |

(Continued)

FOREIGN PATENT DOCUMENTS

| | | |
|---|---|---|
| CN | 102164492 A1 | 8/2011 |
| CN | 102348793 A1 | 2/2012 |

(Continued)

OTHER PUBLICATIONS

Appying [online] retrieved from: http://www.merriam-webster.com/dictionary/applying, on May 21, 2011; 3 pages.*
Cohen (Chemicals from microalgae 1999, CRC Press, pp. 49 and 51 in part).*
Kureshy et al. (Journal of the world aquaculture society 1999, 30(4); 473-480).*
Liao et al. (Rotifer and Microalgae Culture Systems. Proceedings of a US-Asia Workshop. Honolulu, HI, 1991; pp. 135-150.*
English Translation of: (Kanematsu et al. 1989 Nippon Suisan Gakkaishi 55, 1349-1352); 14 pages.*
Tucker (Water Treatment, 1998, Springer, pp. 1-754).*
Rocha et al. (Growth aspects of the marine microalga Nannochloropsis gaditana, 2003, Biomolecular Engineering, vol. 20, pp. 237-242).*

(Continued)

*Primary Examiner* — Brian-Yong Kwon
*Assistant Examiner* — Mark V Stevens
(74) *Attorney, Agent, or Firm* — Carr & Ferrell LLP

(57) ABSTRACT

Systems and methods for maintaining the dominance of *Nannochloropsis* in an algae cultivation system are provided. Exemplary methods include applying an effective amount of a disinfectant to *Nannochloropsis* growing in an algae cultivation system. Another method for maintaining the dominance of *Nannochloropsis* in an algae cultivation system includes adjusting a salinity in the algae cultivation system to between approximately 0.5 PPT and 28 PPT. In a further method, the temperature of the algae cultivation system may be adjusted to between approximately 21 and 32 degrees Celsius ("° C."). According to yet another method for maintaining the dominance of *Nannochloropsis* in an algae cultivation system, a salinity in the algae cultivation system may be adjusted to below that of seawater for a first predetermined period of time, and then the salinity in the algae cultivation system may be adjusted to a higher salinity for a second predetermined period of time.

21 Claims, 4 Drawing Sheets

(56) References Cited

U.S. PATENT DOCUMENTS

| | | | |
|---|---|---|---|
| 7,381,326 B2 | 6/2008 | Haddas |
| 7,391,608 B2 | 6/2008 | Tsai |
| 7,669,780 B2 | 3/2010 | Sugano et al. |
| 7,682,821 B2 | 3/2010 | Woods et al. |
| 7,748,650 B1 | 7/2010 | Sloan |
| 7,770,322 B2 | 8/2010 | Huntley et al. |
| 8,143,051 B2 | 3/2012 | Weissman et al. |
| 8,507,254 B1* | 8/2013 | Abuhasel ............... 435/257.1 |
| 2002/0105855 A1 | 8/2002 | Behnke et al. |
| 2003/0038566 A1 | 2/2003 | Qiu |
| 2003/0116502 A1 | 6/2003 | DeBusk et al. |
| 2003/0140021 A1 | 7/2003 | Ryan et al. |
| 2003/0199490 A1 | 10/2003 | Antoni-Zimmermann et al. |
| 2004/0121447 A1* | 6/2004 | Fournier ............... 435/257.1 |
| 2004/0161364 A1 | 8/2004 | Carlson |
| 2004/0262219 A1 | 12/2004 | Jensen |
| 2005/0064577 A1 | 3/2005 | Berzin |
| 2005/0095569 A1 | 5/2005 | Franklin |
| 2005/0164192 A1 | 7/2005 | Graham et al. |
| 2005/0170479 A1 | 8/2005 | Weaver et al. |
| 2005/0181345 A1 | 8/2005 | Bradbury et al. |
| 2005/0260553 A1 | 11/2005 | Berzin |
| 2005/0273885 A1 | 12/2005 | Singh et al. |
| 2006/0031087 A1 | 2/2006 | Fox et al. |
| 2006/0044259 A1 | 3/2006 | Hotelling et al. |
| 2006/0045750 A1 | 3/2006 | Stiles |
| 2006/0122410 A1 | 6/2006 | Fichtali et al. |
| 2006/0155558 A1 | 7/2006 | Corpening |
| 2006/0166243 A1 | 7/2006 | Su et al. |
| 2006/0192690 A1 | 8/2006 | Philipp |
| 2007/0115626 A1 | 5/2007 | Peng et al. |
| 2007/0155006 A1 | 7/2007 | Levin |
| 2007/0289206 A1 | 12/2007 | Kertz |
| 2008/0118964 A1 | 5/2008 | Huntley et al. |
| 2008/0120749 A1 | 5/2008 | Melis et al. |
| 2008/0155888 A1 | 7/2008 | Vick et al. |
| 2008/0155890 A1 | 7/2008 | Oyler |
| 2008/0160488 A1 | 7/2008 | Younkes et al. |
| 2008/0160591 A1 | 7/2008 | Willson et al. |
| 2008/0160593 A1 | 7/2008 | Oyler |
| 2008/0220486 A1* | 9/2008 | Weiss ............... 435/134 |
| 2008/0293132 A1 | 11/2008 | Goldman et al. |
| 2009/0011492 A1 | 1/2009 | Berzin |
| 2009/0029445 A1 | 1/2009 | Eckelberry et al. |
| 2009/0061928 A1 | 3/2009 | Lee et al. |
| 2009/0126265 A1 | 5/2009 | Rasmussen et al. |
| 2009/0137031 A1 | 5/2009 | Hirabayashi |
| 2009/0148931 A1 | 6/2009 | Wilkerson et al. |
| 2009/0151241 A1 | 6/2009 | Dressler et al. |
| 2009/0162919 A1* | 6/2009 | Radaelli et al. ............ 435/257.6 |
| 2009/0186860 A1 | 7/2009 | Huff et al. |
| 2009/0234146 A1 | 9/2009 | Cooney et al. |
| 2009/0317857 A1* | 12/2009 | Vick et al. ............ 435/29 |
| 2009/0319338 A1 | 12/2009 | Parks et al. |
| 2009/0325270 A1 | 12/2009 | Vick et al. |
| 2010/0022393 A1 | 1/2010 | Vick |
| 2010/0068772 A1 | 3/2010 | Downey |
| 2010/0100520 A1 | 4/2010 | Dargue et al. |
| 2010/0170149 A1 | 7/2010 | Keeler et al. |
| 2010/0170150 A1 | 7/2010 | Walsh, Jr. |
| 2010/0183744 A1 | 7/2010 | Weissman et al. |
| 2010/0196995 A1 | 8/2010 | Weissman et al. |
| 2010/0198659 A1 | 8/2010 | Meltzer et al. |
| 2010/0210003 A1 | 8/2010 | King |
| 2010/0257781 A1 | 10/2010 | Batty et al. |
| 2010/0260618 A1 | 10/2010 | Parsheh et al. |
| 2010/0261922 A1 | 10/2010 | Fleischer et al. |
| 2010/0314324 A1 | 12/2010 | Rice et al. |
| 2010/0323387 A1 | 12/2010 | Bailey et al. |
| 2010/0325948 A1 | 12/2010 | Parsheh et al. |
| 2010/0327077 A1 | 12/2010 | Parsheh et al. |
| 2011/0016773 A1 | 1/2011 | Nichols et al. |
| 2011/0023360 A1 | 2/2011 | Ryan et al. |
| 2011/0051354 A1 | 3/2011 | Fan et al. |
| 2011/0136212 A1 | 6/2011 | Parsheh et al. |
| 2011/0197306 A1 | 8/2011 | Bailey et al. |
| 2011/0258915 A1 | 10/2011 | Subhadra |
| 2011/0287531 A1 | 11/2011 | Hazlebeck |
| 2011/0287544 A1 | 11/2011 | Berzin et al. |
| 2012/0252104 A1 | 10/2012 | Waibel et al. |
| 2012/0272574 A1 | 11/2012 | Parsheh et al. |
| 2013/0130909 A1 | 5/2013 | Vick et al. |

FOREIGN PATENT DOCUMENTS

| | | |
|---|---|---|
| CN | 102459585 A1 | 5/2012 |
| CN | 102575221 A1 | 7/2012 |
| CN | 103649551 A | 3/2014 |
| CN | 103687938 A | 3/2014 |
| EP | 2427551 A1 | 3/2012 |
| HK | 1168381 A1 | 12/2012 |
| JP | 09173050 A * | 7/1997 |
| MX | 201100000934 A1 | 7/2011 |
| MX | 2011008222 A1 | 1/2012 |
| WO | 2004106238 A2 | 12/2004 |
| WO | 2009037683 A1 | 3/2009 |
| WO | 2009149519 A1 | 12/2009 |
| WO | 2010008490 A1 | 1/2010 |
| WO | 2010011335 A1 | 1/2010 |
| WO | 2010090760 A1 | 8/2010 |
| WO | 2010129041 A1 | 11/2010 |
| WO | 2010147648 A1 | 12/2010 |
| WO | 2011002487 A1 | 1/2011 |
| WO | 2012149214 A1 | 11/2012 |
| WO | 2012170737 A1 | 12/2012 |

OTHER PUBLICATIONS

Vinneras et al (The potential for disinfection of separated faecal matter by urea and by peracetic acid for hygienic nutrient recycling, 2003, Bioresources Technology, vol. 89, pp. 155-161).*
CCAP website, f2 media recipe, 2005.*
Palanichamy et al (Observations on the long term preservation and culture of the marine microalga, *Nannochloropsis oculata*, 2004, Journal of Marine Biology Association of India, vol. 46, pp. 98-103).*
Pathak et al. (SEAFDEC.org, 2000, pp. 87-112).*
Fawley et al. (Protist, Jul. 2007, vol. 158, pp. 325-336).*
Science and Technology Focus (Ocean Water: Salinity, 2014).*
Santin-Montanaya, I. Optimal growth of *Dunaliella primolecta* in axenic conditions to assay herbicides, Chemosphere, 66, Elsevier 2006, pp. 1315-1322.
Felix, R. Use of the cell wall-less alga *Dunaliella bioculata* in herbicide screening tests, Annals of Applied Biology, 113, 1988, pp. 55-60.
Janssen, M. Photosynthetic efficiency of *Dunaliella tertiolecta* under short light/dark cycles, Enzyme and Microbial Technology, 29, 2001, pp. 298-305.
Saenz, M.E. Effects of Technical Grade and a Commercial Formulation of Glyphosate on Algal Population Growth, Bulletin of Environmental Contamination Toxicology, 1997, pp. 638-644.
Beckmann et al., "Improvement of light to biomass conversion by de-regulation of light-harvesting protein translation in *Chlamydomonas reinhardtii*," Journal of Biotechnology, vol. 142, No. 1, 2009, pp. 70-77.
International Search Report and Written Opinion of the International Searching Authority mailed Aug. 16, 2012 for Application No. PCT/US2012/041425, filed Jun. 7, 2012.
European Search Report mailed Oct. 5, 2012 in European Patent Application No. 10772376.9, filed May 4, 2010.
Examination Report mailed Feb. 20, 2013 in Australian Application No. 2009274500 filed Jul. 24, 2009.
Notice on the Second Office Action mailed Jun. 20, 2013 in Chinese Application No. 201080012755.3 filed Feb. 4, 2010.
Notice on the Second Office Action mailed Jul. 5, 2013 in Chinese Application No. 201080027531.X filed May 4, 2010.
Examination Report mailed Aug. 22, 2013 in Australian Application No. 2010260530 filed Jun. 15, 2010.
First Office Action mailed Aug. 29, 2013 in Mexican Application No. MX/a/2011/013710 filed Jun. 15, 2010.

(56) References Cited

OTHER PUBLICATIONS

Examination Report mailed Aug. 29, 2013 in European Application No. 10772376.9 filed May 4, 2010.
Examination Report mailed Sep. 19, 2013 in Australian Application No. 2010245255 filed May 4, 2010.
Notice on the Second Office Action mailed Sep. 24, 2013 in Chinese Application No. 200980138072.X filed Jul. 24, 2009.
Ruan, Zuo-xi et al., Effects of Acute Glyphosate Exposure on the Growth and Physiology of *Nostoc Sphaeroides*, an Edible Cyanobacterium of Paddy Rice Fields, Acta Hydrobiologica Sinica, Jul. 2008 vol. 32, No. 4, pp. 462-468.
HCAPLUS abstract 1997; 248650 (1997).
HCAPLUS abstract 2005; 600349 (2005).
HCAPLUS abstract 2007; 1143765 (2007).
Notice on the Second Office Action mailed Oct. 24, 2013 in Chinese Application No. 201080036170.5 filed Jun. 15, 2010.
Office Action mailed Nov. 11, 2013 in Mexican Application No. MX/a/2011/000934 filed Jul. 24, 2009.
Office Action mailed Jan. 30, 2014 in Mexican Application No. MX/a/2011/013710 filed Jun. 15, 2010.
Notice of Allowance mailed Mar. 7, 2014 in Australian Application No. 2010210982 filed Feb. 4, 2010.
Office Action mailed Feb. 12, 2014 in Chinese Application No. 201080012755.3 filed Feb. 4, 2010.
Office Action mailed Mar. 4, 2014 in Chinese Application No. 201080027531.X filed May 4, 2010.
Office Action mailed Mar. 27, 2014 in Israeli Application No. 210805 filed Jul. 24, 2009.
Journal 37/2013, Sep. 13, 2013, Vick et al.
Journal 12/2013, Mar. 22, 2013, Parsheh et al.
Journal 52/2012, Dec. 28, 2012, Weissman et al.
Journal 20/2013, May 17, 2013, Bailey et al.
Christy et al., "Effects of Glyphosate on Growth of *Chlorella*," Weed Science, vol. 29, Issue 1, Jan. 1981, pp. 5-7.
Roessler et al., "Genetic Engineering Approaches for Enhanced Production of Biodiesel Fuel from Microalgae," ACS Symposium Series; American Chemical Society, 1994, pp. 255-270.
Grima et al. "Recovery of Microalgal Biomass in Metabolites: Process Options and Economics," Biotechnology Advances 20, 2003, pp. 491-515.
Knuckey et al. "Production of Microalgal Concentrates by Flocculation and their Assessment as Aquaculture Feeds," Aquacultural Engineering 35, 2006, pp. 300-313.
Csogor et al., "Light Distribution in a Novel Photobioreactor—Modelling for Optimization," Journal of Applied Phycology, vol. 13, 2001, pp. 325-333.
Janssen et al., "Enclosed Outdoor Photobioreactors: Light Regime, Photosynthetic Efficiency, Scale-Up, and Future Prospects," Biotechnology and Bioengineering, vol. 81, No. 2, pp. 193-210, Jan. 2003.
Zittelli et al., "Mass Cultivation of Nannochloropsis Sp. In Annular Reactors," Journal of Applied Phycology, vol. 15, pp. 107-113, Mar. 2003.
Strzepek et al., "Photosynthetic Architecture Differs in Coastal and Oceanic Diatoms," Nature, vol. 431, pp. 689-692, Oct. 2004.
Lee et al., "Isolation and Characterization of a Xanthophyll Aberrant Mutant of the Green Alga *Nannochloropsis oculata*," Marine Biotechnology, 2006, vol. 8, pp. 238-245.
NCBI entry EE109892 (Jul. 2006) [Retrieved from the Internet on Oct. 19, 2009, <http://www.ncbi.nlm.nih.gov/nucest/EE109892?ordinalops=1&itool=EntrezSystem2.Pentrez.Sequence_ResultsPanel.Sequence_RVDocSum>].
Berberoglu et al., "Radiation Characteristics of *Chlamydomonas reinhardtii* CC125 and its truncated chlorophyll antenna transformants tla1, tlaX, and tla1-CW+,"International Journal of Hydrogen Energy, 2008, vol. 33, pp. 6467-6483.
Ghirardi et al., "Photochemical Apparatus Organization in the Thylakoid Membrane of *Hordeum vulgare* wild type and chlorophyll b-less chlorine f2 mutant," Biochimica et Biophysica Act (BBA)—Bioengergetics, vol. 851, Issue 3, Oct. 1986, pp. 331-339 (abstract only).
Steinitz et al., "A mutant of the cyanobacterium *Plectonema boryanum* resistant to photooxidation," Plant Science Letters, vol. 16, Issues 2-3, 1979, pp. 327-335 (abstract only).
Koller et al., "Light Intensity During Leaf Growth Affects Chlorophyll Concentration and CO2 Assimilation of a Soybean Chlorophyll Mutant," Crop Science, 1974, vol. 14, pp. 779-782 (abstract only).
Shikanai et al., "Identification and Characterization of *Arabidopsis* Mutants with Reduced Quenching of Chlorophyll Fluorescence," Plant and Cell Physiology, 1999, vol. 40, No. 11, pp. 1134-1142 (abstract only).
Andersen, "Algal Culturing Techniques," 2005, p. 208.
Ben-Amotz, Ami. "Large-Scale Open Algae Ponds," presented at the NREL-AFOSR Joint Workshop on Algal Oil for Get Fuel Production in Feb. 2008.
Ebeling et al., "Design and Operation of a Zero-Exchange Mixed-Cell Raceway Production System," 2nd Int'l Sustainable Marine Fish Culture Conference and Workshop, Oct. 2005.
Ebeling et al., "Mixed-Cell Raceway: Engineering Design Criteria, Construction, and Hydraulic Characterization," North American Journal of Aquaculture, 2005, 67: 193-201 (abstract only).
Labatut et al., "Hydrodynamics of a Large-Scale Mixed-Cell Raceway (MCR): Experimental Studies," Aquacultural Engineering vol. 37, Issue 2, Sep. 2007, pp. 132-143.
Kizilisoley et al., "Micro-Algae Growth Technology Systems," Presented by Selim Helacioglu, Soley Institute, 2008.
Kent BioEnergy, "Fish Farm Empties Its Ponds to Grow Algae for Biofuels," Apr. 17, 2009 (http://www-csgc.ucsd.edu/newsroom/newsreleases/2009/algaeforbiofuls.html).
Hoyt et al., "Waves on Water Jets," J. Fluid Mech., 1977, vol. 83, Part 1, pp. 119-127.
Dodd, "Elements of Pond Design and Construction," CRC Handbook of Microalgal Mass Culture, Richmond, ed., Boca Raton, FL.: CRC Press, 1986, pp. 265-283, see entire document, especially Fig. 1; p. 268, para. 3 to p. 269, para. 1; p. 270, para. 1.
Mitra et al., "Optical Properties of Microalgae for Enhanced Biofuels Production," Optics Express, Dec. 2008, vol. 16, No. 26.
Rodolfi et al., "Microalgae for Oil: Strain Selection, Induction of a Lipid Synthesis and Outdoor Mass Cultivation in a Low-Cost Photobioreactor," Biotechnology and Bioengineering, 2008, vol. 102, No. 1, pp. 100-112.
International Search Report mailed Sep. 16, 2009 for Application No. PCT/US2009/004296, filed Jul. 24, 2009.
Written Opinion of the International Searching Authority mailed Sep. 16, 2009 for Application No. PCT/US2009/004296, filed Jul. 24, 2009.
Office Action mailed Nov. 14, 2012 in China Patent Application No. 200980138072.X, filed Jul. 24, 2009.
Official Action mailed Jul. 10, 2012 in Mexico Patent Application No. MX/a/2011/000934, filed Jul. 24, 2009.
Official Action mailed Mar. 5, 2013 in Mexico Patent Application No. MX/a/2011/000934, filed Jul. 24, 2009.
Duarte et al., "Glyphosate (GP) Effects with Emphasis on Aquatic Organisms," Colunbia Orinoquia, ISSN: 0121-3709, pp. 70-100, 2004.
Technical Card: Glyphosate, Document filed for the Pesticide Action Network and the Alternatives Thereof, for Latin America (RAP-AL)-Communications and Administration Office, Apr. 2008.
Republic of Columbia Department of Environment, Housing and Territorial Development, Resolution (1009), published Jun. 17, 2008. (36 pages).
International Search Report and Written Opinion of the International Searching Authority mailed May 3, 2010 for Application No. PCT/US2010/000346, filed Feb. 4, 2010.
Patent Examination Report No. 1 mailed Jan. 9, 2013 in Australia Patent Application 2010210982, filed Feb. 4, 2010.
First Office Action mailed Nov. 5, 2012 in China Patent Application No. 201080012755.3, filed Feb. 4, 2010.
Official Action mailed Sep. 17, 2012 in Mexico Patent Application No. MX/a/2011/008222, filed Feb. 4, 2010.

(56) References Cited

OTHER PUBLICATIONS

International Search Report and Written Opinion of the International Searching Authority mailed Aug. 30, 2010 for Application No. PCT/US2010/001731, filed Jun. 15, 2010.

Notice on the First Office Action mailed Dec. 14, 2012 in Chinese Application No. 201080036170.5 filed Jun. 15, 2010.

International Search Report and Written Opinion of the International Searching Authority mailed Aug. 19, 2010 for Application No. PCT/US2010/001755, filed Jun. 16, 2010.

International Search Report and Written Opinion of the International Searching Authority mailed Jul. 31, 2012 for Application No. PCT/US2012/035290, filed Apr. 26, 2012.

International Search Report and Written Opinion of the International Searching Authority mailed Jul. 30, 2010 for Application No. PCT/US2010/001315, filed May 4, 2010.

First Office Action mailed Oct. 25, 2012 in China Patent Application No. 201080027531.X, filed May 4, 2010.

Extended European Search Report mailed Oct. 5, 2012 in European Patent Application 10772376.9, filed on May 4, 2010.

Polle et al., "tla1, a DNA insertional transformant of the green alga *Chlamydomonas reinhardtii* with a truncated light-harvesting chlorophyll antenna size," Planta, vol. 217, No. 1, May 2003, pp. 49-59.

Lawrence et al., "Variation in Plants Regenerated from Vacuolate and Evacuolate Protoplasts," Plant Science, vol. 50, No. 2, 1987, pp. 125-132.

\* cited by examiner

SYSTEMS AND METHODS FOR MAINTAINING THE DOMINANCE OF *NANNOCHLOROPSIS* IN AN ALGAE CULTIVATION SYSTEM

BACKGROUND OF THE INVENTION

1. Field of the Invention

This invention relates to algae cultivation systems, and more specifically to systems and methods for maintaining the dominance of *Nannochloropsis* in an algae cultivation system.

2. Description of Related Art

*Nannochloropsis* cultures are subject to contamination by competing species and predators. Optimizing an algae cultivation system for the growth of *Nannochloropsis* to increase its resistance to competing species and predators results in fewer collapses, or crashes, of the *Nannochloropsis* culture. The maintenance of a stable mass culture of *Nannochloropsis* maximizes the accumulation of biomass. This accumulation of biomass is highly desirable in the production of biofuels and higher value products, such as, but not limited to, animal feed, fish meal formulations, carotenoids, polyunsaturated fatty acids ("PUFAs"), and products for the cosmetic and pharmaceutical industries. The exemplary embodiments described herein accomplish these objectives.

SUMMARY OF THE INVENTION

Systems and methods for maintaining the dominance of *Nannochloropsis* in an algae cultivation system are provided. Exemplary methods include adjusting a salinity in the algae cultivation system to between approximately 0.5 Parts Per Thousand ("PPT") and 28 PPT.

Another exemplary method includes applying an effective amount of a disinfectant to *Nannochloropsis* growing in an algae cultivation system. The disinfectant may be sodium hypochlorite and the effective amount of sodium hypochlorite results in an approximate initial concentration of between 0.1 milligrams/liter and 40 milligrams/liter of sodium hypochlorite in the algae cultivation system. A further method may include applying a shock amount of sodium hypochlorite that results in an approximate initial concentration of between 40 milligrams/liter and 80 milligrams/liter or higher of sodium hypochlorite in the algae cultivation system.

Other exemplary methods for maintaining the dominance of *Nannochloropsis* in an algae cultivation system include adjusting a salinity in the algae cultivation system to between approximately 0.5 PPT and 28 PPT, and applying an effective amount of a disinfectant to *Nannochloropsis* growing in the algae cultivation system. In some embodiments, the disinfectant is sodium hypochlorite, and the effective amount of the sodium hypochlorite results in an approximate initial concentration of between 0.1 milligrams/liter and 40 milligrams/liter of sodium hypochlorite in the algae cultivation system.

According to yet another exemplary method for maintaining the dominance of *Nannochloropsis* in an algae cultivation system, a salinity in the algae cultivation system is adjusted to below that of seawater (e.g., approximately 5-10 PPT) for a first predetermined period of time, and then the salinity in the algae cultivation system is adjusted to approximately 60% to 125% that of seawater (e.g., approximately 20-45 PPT) for a second predetermined period of time. The method may further include applying an effective amount of a disinfectant to *Nannochloropsis* growing in the algae cultivation system. Either or both of these methods may also include adjusting temperature within the algae cultivation system to between approximately 21° C. and 32° C.

Various exemplary embodiments may include a system for maintaining dominance of *Nannochloropsis* in an algae cultivation system. The system may comprise a processor, and a computer readable storage medium having instructions for execution by the processor. The instructions for execution by the processor cause the processor to maintain dominance of the *Nannochloropsis* in the algae cultivation system. The processor is connected to the computer readable storage medium. The processor executes the instructions on the computer readable storage medium to adjust a salinity in the algae cultivation system to approximately 5-10 PPT for a first predetermined period of time and to adjust the salinity in the algae cultivation system to approximately 20-45 PPT for a second predetermined period of time. The processor may execute other instructions described herein and remain within the scope of contemplated embodiments.

DETAILED DESCRIPTION OF THE INVENTION

By utilizing the unexpected discoveries that *Nannochloropsis* dominates a lower salinity environment and recovers from a high exposure to a disinfectant in comparison to its competing species (or invaders) and predators, the exemplary systems and methods described herein optimize an algae cultivation system for the growth of *Nannochloropsis*. Embodiments described herein increase the resistance of *Nannochloropsis* to competing species and predators and results in fewer collapses, or crashes, of the *Nannochloropsis* culture. Further, the various systems and methods described herein maximize the production of biomass by *Nannochloropsis*, which is highly desirable for large volume applications, such as for the production of biofuels.

Figure 1:
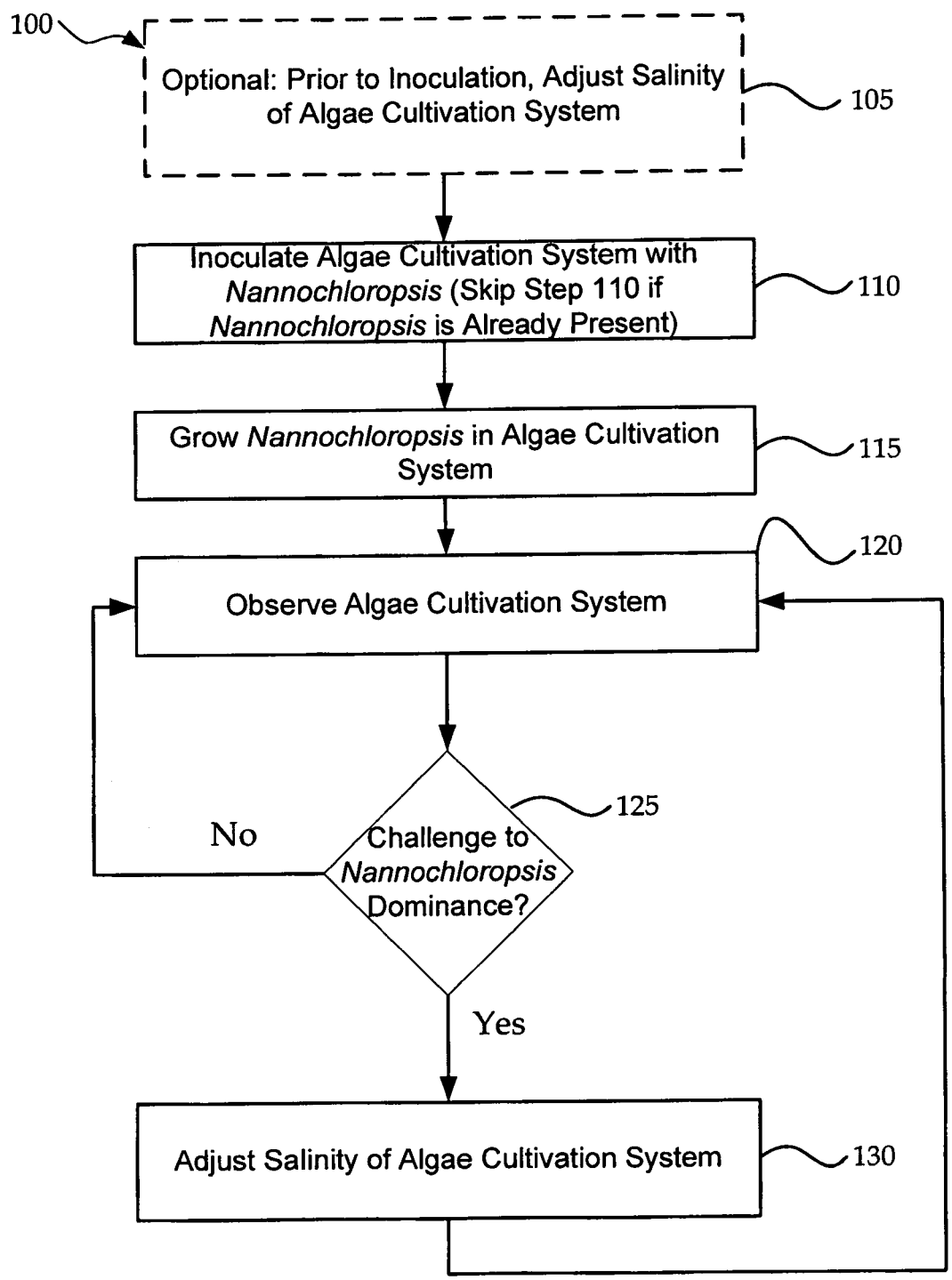
FIG. 1 shows a flow chart for an exemplary method of using salinity to maintain the dominance of *Nannochloropsis* in an algae cultivation system.

FIG. 1 shows a flow chart for an exemplary method 100 of using salinity to maintain the dominance of *Nannochloropsis* in an algae cultivation system.

At optional step 105, before the algae cultivation system is inoculated with *Nannochloropsis*, the salinity of the algae cultivation system may be adjusted to: at, above, or below the salinity of seawater. The salinity of seawater is usually between 35 and 42 Parts Per Thousand ("PPT"), which typically represents the total dissolved solids or total dissolved salts ("TDS") in an aqueous environment. According to one embodiment, the salinity of the algae cultivation system is adjusted to approximately 22-24 PPT. The salinity of the algae cultivation system may be adjusted via the inlet mix of water streams that feed into the algae cultivation system. For example, by adjusting the relative flow of seawater and fresh water feeding into the algae cultivation system, the salinity of the algae cultivation system may be adjusted from about 0.5

PPT (i.e. the approximate salinity of many fresh ground and surface waters, or of even lower total dissolved solids waters that have been supplemented with the minimal amounts of minerals and nutrients to support growth of typical fresh water algae) to 35 PPT (i.e. the approximate salinity of seawater) to 150 PPT and above (i.e. the salinity may increase beyond that of seawater, up to the maximum solubility of salt, due to water evaporation). Various streams of water with different salinities (e.g., brackish water, well water, city water, irrigation water, agricultural runoff, etc.) may be mixed with seawater to adjust the salinity. This step may be performed in addition to step 130 as described herein.

Unlike most microorganisms, *Nannochloropsis* may grow in a wide range of salt concentrations. Additionally, the following experiments conducted by the inventors in the laboratory show the relationship of *Nannochloropsis* productivity as a function of salinity:

| Salinity (PPT) | Salinity (Percent of Sea Water) | Mean Productivity (Milligrams of Biomass per Liter per Day) |
|---|---|---|
| 3.00 | 8.5 | 650 |
| 8.75 | 25 | 690 |
| 17.50 | 50 | 704 |
| 26.25 | 75 | 688 |
| 35.00 | 100 | 704 |
| 43.75 | 125 | 639 |

Additionally, the following experiments conducted by the inventors in outdoor open ponds show the relationship of *Nannochloropsis* productivity as a function of salinity:

| Salinity (PPT) | Salinity (Percent of Seawater) | Productivity (Percent of Two-Thirds Seawater Control) |
|---|---|---|
| 0.5 | 1.5 | 50 |
| 1.5 | 4 | 60 |
| 5 | 15 | 85-95 |
| 22 | 67 | 100 |
| 35 | 100 | 80-120 |

Other significant uses of low salinity media were confirmed by outdoor experiments. Salinities below 10 PPT increased the tolerance of *Nannochloropsis* to warm temperatures leading to more stable and productive cultures. These low salinities also reduced fouling [i.e. the attachment of inorganic and organic material (alive or not) to the pond surfaces (sides, bottoms, mixers, any surface in the water)]. The fouling was reduced to almost unobservable levels which made cleaning of the ponds essentially unnecessary. At the low salinities, settling of organic matter to the pond bottom was reduced to insignificant levels throughout the cultivation period, even at the lowest mixing speeds. Both the reduced fouling and reduced settling of organic material significantly enhanced *Nannochloropsis* dominance by reducing predation and competing species that would otherwise arise from fouling and sedimentation.

At step 110, the algae cultivation system is inoculated with *Nannochloropsis* (note: step 110 may be skipped if *Nannochloropsis* is already present, e.g., an existing pond, vessel, photobioreactor, etc. with *Nannochloropsis*). According to various exemplary embodiments, the algae cultivation system may be an open pond, a closed pond and/or a photobioreactor. Further, the *Nannochloropsis* culture may comprise one or more strains of the genus *Nannochloropsis*. Outdoor *Nannochloropsis* cultures may be started with the addition of an initial, small amount of pure unialgal (virtually free from unwanted contaminant organisms) *Nannochloropsis*. Such an inoculum may be generated in a controlled environment, such as in a laboratory or in a closed system. The inoculum may be introduced into a larger volume of water that may have a predetermined salinity (e.g., using step 105 as described herein) chosen to be optimal for the *Nannochloropsis* growth and/or chosen to be suboptimal for competing strains.

At step 115, the *Nannochloropsis* is grown in the algae cultivation system. According to various embodiments, the *Nannochloropsis* culture may require light (natural or artificially supplied) for growth, as well as nutrients. Other parameters such as pH should be within acceptable ranges. The basic elements typically required for *Nannochloropsis* growth may include carbon, oxygen, hydrogen, nitrogen, sulfur, phosphorous, potassium, magnesium, iron and traces of several other elements.

The required nutrients for *Nannochloropsis* growth may be contained in the water, supplied subsequently in dilution waters, or supplied independently of the dilution waters, in a concentration sufficient to allow *Nannochloropsis* to grow and reach a desired final density. The amount of nutrients needed to yield a prescribed *Nannochloropsis* density may be determined by the cell quota for that nutrient. That is, by the per cent of the algal dry mass that is comprised of the element contained in the nutrient. The inverse of the cell quota is called the algae growth potential for that nutrient or element. For instance, if the desired final density is 1 gram/liter and the *Nannochloropsis* strain under consideration contains ten percent (10%) nitrogen in its biomass (i.e., a cell quota of 0.1), then the initial concentration of the atomic nitrogen in the culture should be at least 0.1 gram/liter. The same calculation may be performed for all nutrients to establish their initial concentration in the culture.

In various embodiments, a wide variety of systems utilized for the mass culturing of algae may be optimized for *Nannochloropsis* growth. The time-averaged light intensity to which *Nannochloropsis* may be exposed may be adjusted by changes in the mixing intensity and in the optical depth of the apparatus. In panel-shaped modular photobioreactors, the latter may be performed by controlling the distance between two consecutive panels. On the other hand, the optical depth in open ponds may be the depth of the pond. Similarly, the temperature in closed photobioreactors may be precisely controlled by means of indirect heat exchange. In open ponds, the temperature may be controlled by adjusting culture depth. After two to ten days, *Nannochloropsis* may reach a productive operating density depending on light intensity, temperature, and the starting inoculum size.

Once the *Nannochloropsis* is grown to a desired density, according to some embodiments, it may either be removed (and a new culture may be started with a new inoculum), or it may be diluted according to a prescribed schedule or rate. In the first case, culturing may be performed in a batch mode and may require frequent re-inoculation. In the latter case, culturing may be performed in a continuous or a semi-continuous fashion, depending on the way the dilution is performed. For example, assuming that the desired dilution rate is fifty percent (50%) per day of the culture volume, culture dilution may take place in one or more of several techniques. Culture dilution may take place continuously over the day (or over part of the day) at a constant or at a variable rate. Culture dilution may alternatively take place semi-continuously once a day (i.e., fifty percent (50%) of the culture is removed and replaced with a new growth medium in a short period of time every day); semi-continuously twice a day (i.e., twenty-five percent (25%) of the culture is removed each time at two different times every day); or semi-continuously at any other desired frequency over the day. In some embodiments, culture dilution may comprise removing the *Nannochloropsis* culture medium from the growth system—whether this is in an open pond or in a closed photobioreactor—and replacing this portion with fresh medium, which may contain all of the nutrients in the quantity sufficient for the growth of the *Nannochloropsis* between two consecutive dilutions.

At step 120, after the algae cultivation system is inoculated with *Nannochloropsis* and the *Nannochloropsis* is grown to a desired density (e.g., as described in connection with step 110 and step 115), the algae cultivation system may be observed (e.g., visually with a naked eye, microscopically, and/or analytically, including the taking and analysis of samples). Such observations or sampling may take place every minute, hourly, daily, every other day, three times a week, weekly, and/or on any other suitable basis. In connection with this process, one or more determinations may be made as to a relative level or amount of predators and/or invaders in comparison to an actual and/or desired density or dominance of *Nannochloropsis*.

At step 125, a determination is made whether *Nannochloropsis* dominance in the algae cultivation system is being challenged by predators and/or invaders. Based upon this determination, a decision may be made whether to adjust the salinity of the algae cultivation system to below that of seawater. If the level or amount of predators and/or invaders is less than a prescribed level, the salinity of the algae cultivation system may not require the adjustment described in connection with step 130 and the algae cultivation system may continue to be observed as described in connection with step 120. Alternatively, the salinity of the algae cultivation system may be adjusted upward and the algae cultivation system may continue to be observed as described in connection with step 120.

At step 130, if the level or amount of predators and/or invaders exceeds an actual or desired level, the salinity of the algae cultivation system may be adjusted to below that of seawater. According to various embodiments, an initial salinity in the algae cultivation system may range between 0.5 PPT and 60 PPT. For example, to maintain the dominance of *Nannochloropsis* in the algae cultivation system, approximately two-thirds (⅔) seawater having an approximate salinity of 35 PPT may be mixed with approximately one-third (⅓) fresh water having an approximate salinity of 0 PPT to result in a salinity of approximately 22 PPT to 24 PPT. Other ratios of seawater and fresh water may be used to achieve a desired salinity (e.g., between approximately 5 PPT and 28 PPT) in the algae cultivation system. According to alternative embodiments, a desired salinity may be achieved by other means, such as by adding salt to fresh water in the required amount.

In some embodiments, if semi-continuous or continuous culturing is utilized, the *Nannochloropsis* culture may be regularly diluted. Thus, a portion of the culture may be replaced with new water that may have the same nutrient concentration as the initial medium utilized for inoculation. Alternatively, the nutrients may be added separately. The salinity of the new medium may be adjusted by controlling the ratio of seawater to fresh water (or by adding the required amount of salt to fresh water or by other similar methods) to keep the salinity of the algae cultivation system after the dilution in the approximate range of 0.5 PPT to 35 PPT. For example, if the salinity of the algae cultivation system before dilution has increased to 30 PPT because of evaporation and the desired dilution rate is fifty percent (50%), then the new medium may need to have a salinity of approximately 20 PPT to achieve a salinity of 25 PPT after the dilution. This may be accomplished manually or by automatic control systems.

According to an alternative embodiment, exploitation of the salinity tolerance of *Nannochloropsis* may maintain *Nannochloropsis* dominance. By continuously or periodically varying the salinity of the algae cultivation system between 1 percent (1%) and one-hundred twenty-five percent (125%) of the salinity of normal seawater, microorganisms that could otherwise dominate the algae cultivation system at a particular salinity may be selectively outcompeted by *Nannochloropsis*. Changing the salinity may be accomplished in many ways including, but not limited to, using water which is of a greater (or a lesser) salinity than that of the pond medium for the water to make up for losses (evaporation, blow down, etc.) to slowly change the salinity of the growth medium, or to refill a pond, after harvesting some or all of it with recycled effluent from another pond of a different salinity. In this way, a low salinity medium could be cycled around a pond system.

If step 130 is performed, post-treatment observations may be made as described in connection with step 120. Generally, if the density or dominance of *Nannochloropsis* increases, one may assume that the performing of step 130 was effective (i.e. an effective protocol).

Figure 2:
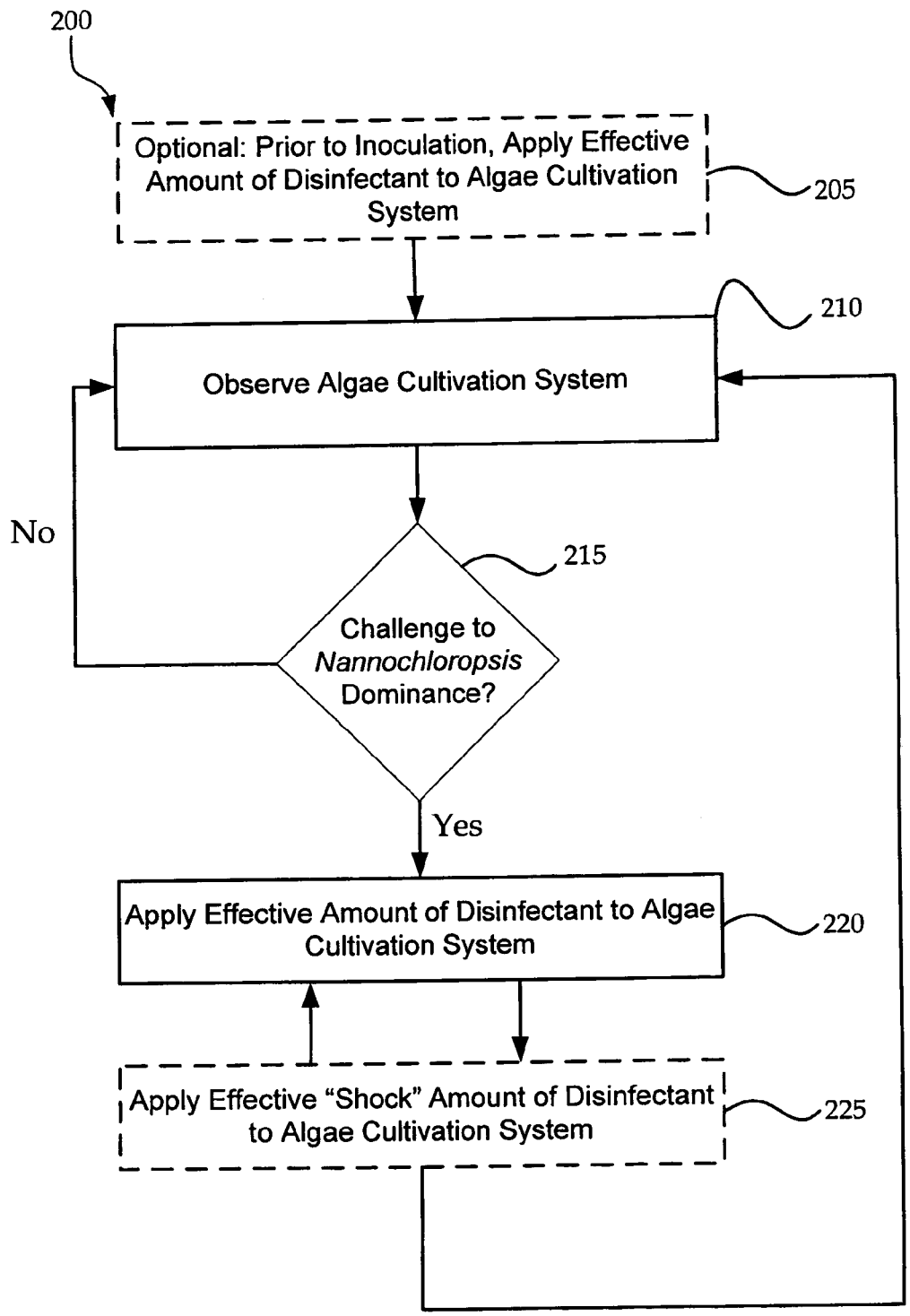
FIG. 2 shows a flow chart for an exemplary method of using disinfectant concentrations to maintain the dominance of *Nannochloropsis* in an algae cultivation system.

FIG. 2 shows a flow chart for an exemplary method 200 of using disinfectant concentrations to maintain the dominance of *Nannochloropsis* in an algae cultivation system.

In some embodiments, *Nannochloropsis* dominance may be maintained in an outdoor system by exploiting the tolerance of *Nannochloropsis* to common chemical disinfectants such as chlorine, chlorine gas, chloride salts, iodine, other halogens, ozone and/or other disinfectants. Experiments conducted by the inventors demonstrate that *Nannochloropsis* is tolerant to concentrations of disinfectants that are significantly higher than those concentrations of disinfectants commonly utilized for general sterilization. Specifically, sodium hypochlorite concentrations for general sterilization purposes are generally maintained between approximately 1 milligram/liter and 10 milligrams/liter. The following results show the extremely high tolerance of *Nannochloropsis* to the various concentrations of sodium hypochlorite:

| Sodium Hypochlorite Concentration (Milligrams/Liter) in an Algae Cultivation System (daily addition) | Mean Productivity of *Nannochloropsis* (Milligrams/Liter/Day) |
| --- | --- |
| 0 | 620 |
| 20 | 570 |
| 40 | 460 |
| 80 | 0 |

The above results are based on adding sodium hypochlorite to *Nannochloropsis* in an algae cultivation system every day to maintain the chlorine concentration at the desired level. As shown by the above data, *Nannochloropsis* is resistant to sodium hypochlorite concentrations that are approximately one order of magnitude higher than the sodium hypochlorite concentrations commonly used for sterilization. In particular, the concentration of the disinfectant in the algae cultivation system may be continuously or intermittently kept at a relatively high level, between 0.1 milligrams/liter and 40 milligrams/liter, which prevents other microorganisms from growing in the same algae cultivation system. Alternatively, a large sporadic injection (e.g., a "shock" amount of sodium hypochlorite that results in an approximate initial concentration of between 40 milligrams/liter and 80 milligrams/liter or higher of sodium hypochlorite in the algae cultivation system) of a disinfectant may kill most, if not all of the competing organisms and allow *Nannochloropsis* to recover in two to three days. Further, administering a "shock" treatment that includes a combination of disinfectants may also kill most, if not all of the competing organisms and allow *Nannochloropsis* to recover.

Referring again to exemplary method 200, at optional step 205, before the algae cultivation system is inoculated with *Nannochloropsis*, an effective amount of a disinfectant may be applied to the algae cultivation system. Such a step may be viewed as a prophylactic measure. Applying an effective amount of a disinfectant such as sodium hypochlorite to the algae cultivation system may result in a sodium hypochlorite concentration of between approximately 0.1 milligrams/liter to 40 milligrams/liter. This step may be performed in addition to steps 220 and 225 as described herein.

At step 210, after the algae cultivation system is inoculated with *Nannochloropsis* and the *Nannochloropsis* is grown to a desired density (e.g., as described in connection with FIG. 1 step 110 and step 115), the algae cultivation system may be observed (e.g., visually with a naked eye, microscopically, and/or analytically, including the taking and analysis of samples). Such observations or sampling may take place every minute, hourly, daily, every other day, three times a week, weekly, and/or on any other suitable basis. In connection with this process, one or more determinations may be made as to a relative level or amount of predators and/or invaders in comparison to an actual and/or desired density or dominance of *Nannochloropsis*.

At step 215, a determination is made whether *Nannochloropsis* dominance in the algae cultivation system is being challenged by predators and/or invaders. Based upon this determination, a decision may be made whether to apply an effective amount of disinfectant and/or an effective shock amount of disinfectant to the algae cultivation system. If the level or amount of predators and/or invaders is less than a prescribed level, the algae cultivation system may not require the application of disinfectant and the algae cultivation system may continue to be observed as described in connection with step 210.

At step 220, if the level or amount of predators and/or invaders exceeds an actual or desired level, an effective amount of a disinfectant may be applied to the algae cultivation system. An effective amount of a disinfectant may be continuously or intermittently applied to the algae cultivation system. According to one embodiment, applying an effective amount of a disinfectant such as sodium hypochlorite to the algae cultivation system may result in a sodium hypochlorite concentration of between approximately 0.1 milligrams/liter to 40 milligrams/liter.

At alternative step 225, if the level or amount of predators and/or invaders exceeds an actual or desired level, an effective "shock" amount of a disinfectant may be applied to the algae cultivation system. An effective shock amount of a disinfectant may be continuously or intermittently applied to the algae cultivation system. An unexpected result observed via the experiments described herein is that *Nannochloropsis* cultures exposed to extremely high levels of sodium hypochlorite (above 80 milligrams/liter) recover (i.e., the *Nannochloropsis* cultures were not killed), provided the exposure to the disinfectant is not prolonged. In particular, when a high concentration of sodium hypochlorite (e.g., at least 80 milligrams/liter) is applied to the algae cultivation system, the *Nannochloropsis* may display zero productivity in the first two days following the administration of the sodium hypochlorite before it exhibits productivity in the following days until normal productivity is restored. Note: steps 215 and 220 may be performed in alternating or rotating fashion, provided chlorine and/or salinity are properly observed.

If step 220 and/or step 225 are performed, post-treatment observations may be made as described in connection with step 210. Generally, if the density or dominance of *Nannochloropsis* increases, one may assume the step or steps performed was effective (i.e. an effective protocol). If the density or dominance of *Nannochloropsis* decreases, one may assume the step or steps performed was ineffective (i.e. an ineffective protocol).

According to an alternative embodiment, the addition of the disinfectant to the culture may be continual by applying it every day or every other day or on some other predetermined schedule.

Figure 3:
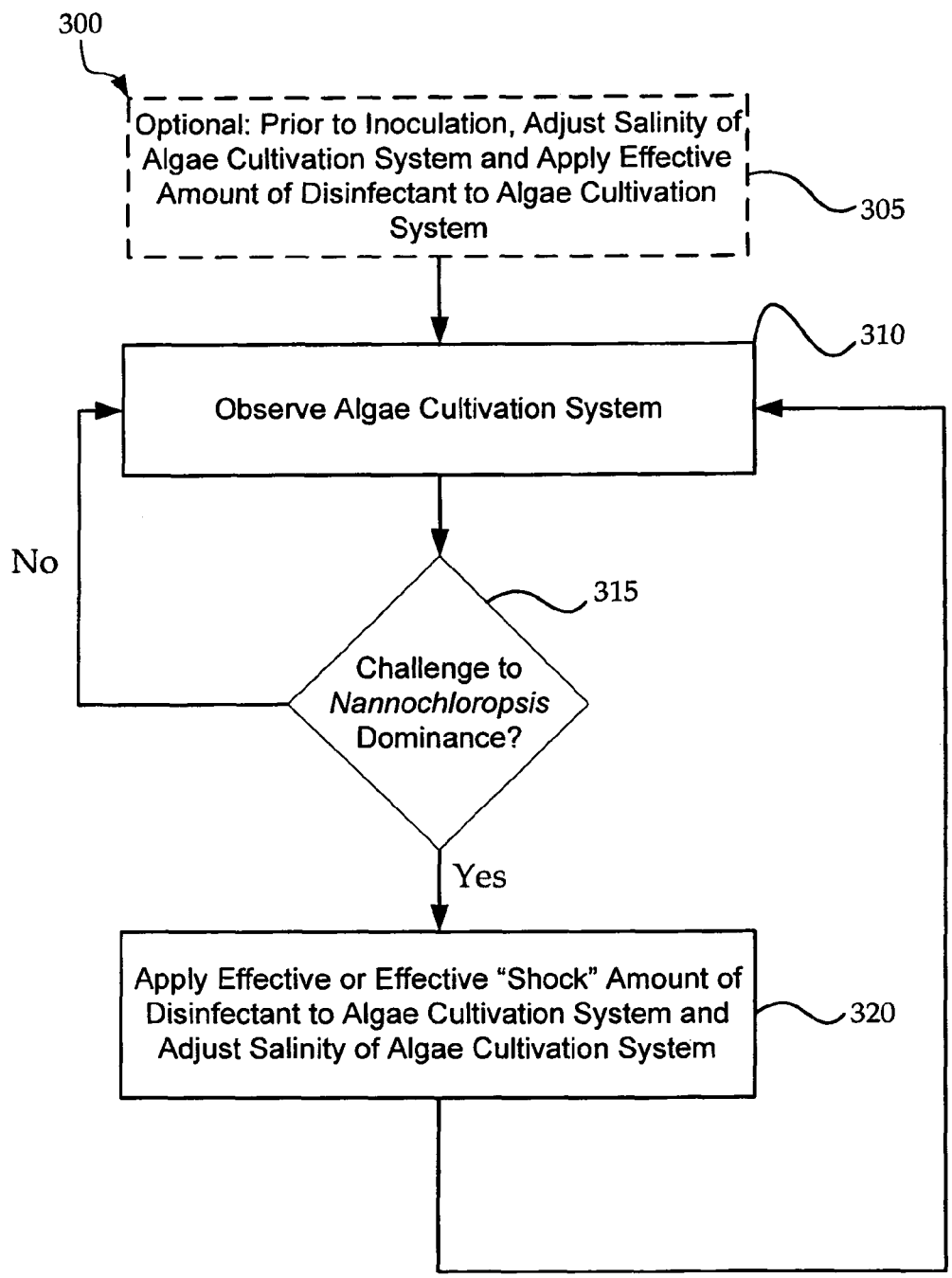
FIG. 3 shows a flow chart for an exemplary method of using salinity and chlorine concentration to maintain the dominance of *Nannochloropsis* in an algae cultivation system.

FIG. 3 shows a flow chart for an exemplary method 300 of using salinity and chlorine concentration to maintain the dominance of *Nannochloropsis* in an algae cultivation system.

At optional step 305, before the algae cultivation system is inoculated with *Nannochloropsis*, the salinity of the algae cultivation system may be adjusted to: at, above, or below, the salinity of seawater. According to one embodiment, the salinity of the algae cultivation system is adjusted to approximately 0.5-28 PPT. The salinity of the algae cultivation system may be adjusted as described in connection with step 105 (FIG. 1) herein. Also at optional step 305, an effective amount of a disinfectant may be applied to the algae cultivation system. Applying an effective amount of a disinfectant such as sodium hypochlorite to the algae cultivation system may result in a sodium hypochlorite concentration of between approximately 0.1 milligrams/liter to 40 milligrams/liter. Step 305 may be performed in addition to step 320 as described herein.

At step 310, after the algae cultivation system is inoculated with *Nannochloropsis* and the *Nannochloropsis* is grown and/or grown to a desired density (e.g., as described in connection with FIG. 1 step 110 and step 115), the algae cultivation system may be observed. The algae cultivation system may be observed visually with a naked eye, microscopically, and/or analytically, including the taking and analysis of samples. Such observations or sampling may take place every minute, hourly, daily, every other day, three times a week, weekly, and/or on any other suitable basis.

At step 315, a determination is made whether *Nannochloropsis* dominance in the algae cultivation system is being challenged by predators and/or invaders. Based upon this determination, a decision may be made whether to apply an effective amount of disinfectant, an effective shock amount of disinfectant and/or adjust the salinity of the algae cultivation system to below that of seawater. If the level or amount of predators and/or invaders is less than a prescribed level, the algae cultivation system may not require such adjustments and the algae cultivation system may continue to be observed as described in connection with step 310. Alternatively, the salinity of the algae cultivation system may be adjusted upward and the algae cultivation system may continue to be observed as described in connection with step 315.

At step 320, if the level or amount of predators and/or invaders exceeds an actual or desired level, the salinity of the algae cultivation system may be adjusted to below that of seawater as described in connection with step 130 (FIG. 1) herein. Also at step 320, an effective amount of a disinfectant or an effective shock amount of a disinfectant may be applied to the algae cultivation system as described in connection with step 220 (FIG. 2) or step 225 (FIG. 2) herein.

If step 320 is performed, post-treatment observations may be made as described in connection with step 310. Generally, if the density or dominance of *Nannochloropsis* increases, one may assume the step(s) performed was effective (i.e. an effective protocol). If the density or dominance of *Nannochloropsis* decreases, one may assume the step(s) performed was ineffective (i.e. an ineffective protocol).

Figure 4:
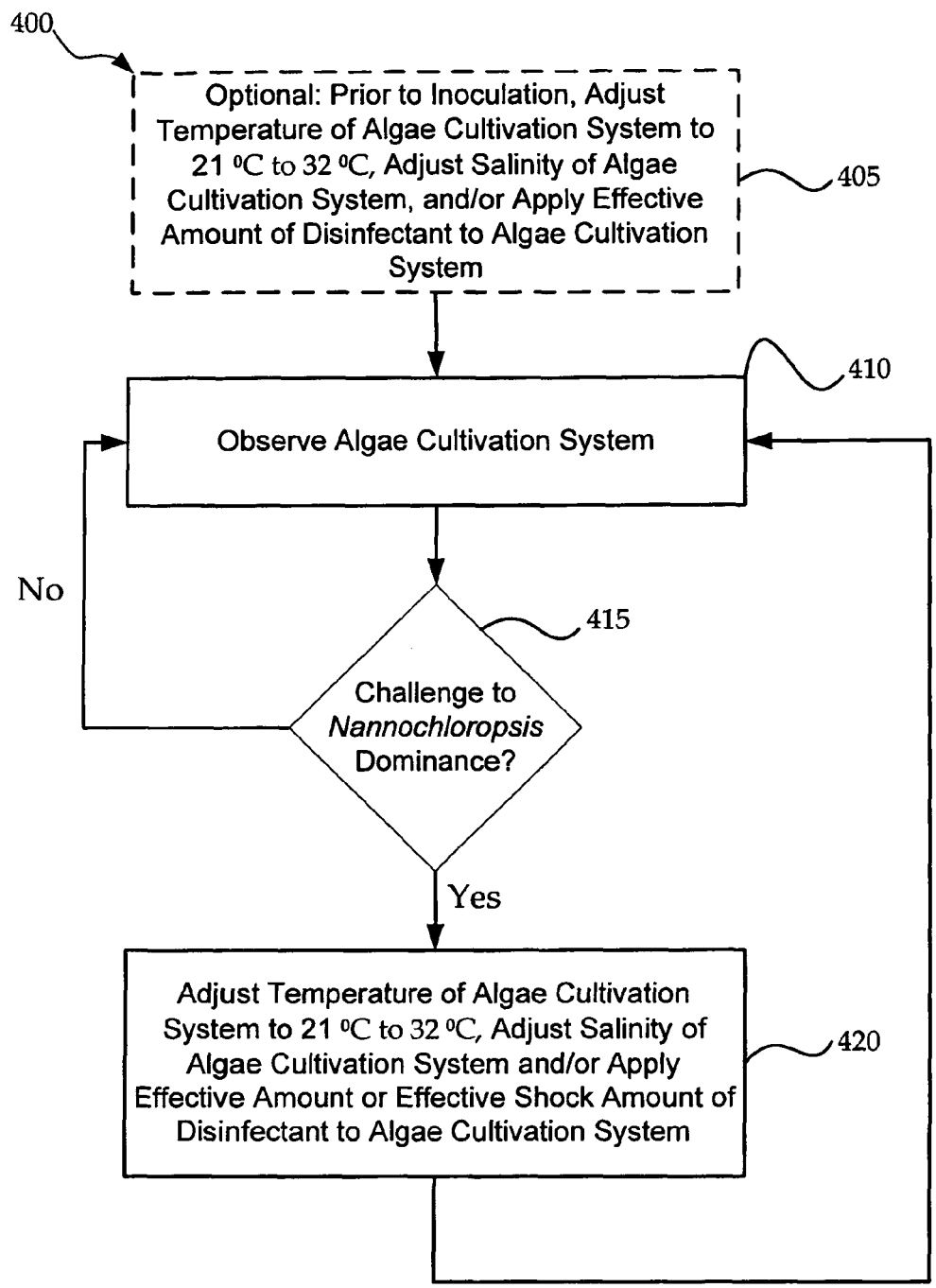
FIG. 4 shows a flow chart for an exemplary method of using salinity and/or chlorine concentration (with or without changing the temperature level) to maintain the dominance of *Nannochloropsis* in an algae cultivation system.

FIG. 4 shows a flow chart for an exemplary method 400 of using salinity and/or chlorine concentration with or without changing temperature level to maintain the dominance of *Nannochloropsis* in an algae cultivation system.

In some embodiments, the dominance of *Nannochloropsis* is maintained by controlling the temperature of the algae cultivation system where the *Nannochloropsis* is growing. The following results obtained by the inventors show *Nannochloropsis* productivity as a function of temperature:

| Temperature in the Algae Cultivation System (Celsius ° C.) | Mean Productivity (Milligrams/Liter/Day) |
| --- | --- |
| 15 | 342 |
| 20 | 483 |
| 25 | 826 |
| 35 | 431 |
| 40 | 17 |

The above data suggests that *Nannochloropsis* produces the most biomass when the temperature is maintained between approximately 21° C. and 32° C. If the temperature in the algae cultivation system is kept within this range, *Nannochloropsis* may outcompete other microorganisms that live in lower or higher optimal growing temperatures.

At optional step 405, before the algae cultivation system is inoculated with *Nannochloropsis*, the temperature of the algae cultivation system may be adjusted to between approximately 21° C. and 32° C. The temperature may be controlled or adjusted in various growth systems by using different means. For example, in open ponds, the temperature may be controlled by adjusting the pond depth. Depths greater than 30 centimeters (cm) are typically sufficient to keep the algae cultivation system such that the *Nannochloropsis* may grow below 35° C. in hot climates, such as those found in tropical geographical regions. In closed photobioreactors, for example, the temperature may be controlled or adjusted by means of heat exchangers or cooling water or other artificial devices. Also at optional step 405, the salinity of the algae cultivation system may be adjusted as described in connection with step 105 (FIG. 1) herein. According to a further embodiment, at optional step 405, an effective amount of a disinfectant may be applied to the algae cultivation system as described in connection with step 205 (FIG. 2) herein. Step 405 may be performed in addition to step 420 as described herein.

At step 410, after the algae cultivation system is inoculated with *Nannochloropsis* and the *Nannochloropsis* is grown and/or grows to a desired density (e.g., as described in connection with FIG. 1 step 110 and step 115), the algae cultivation system may be observed as described herein in connection step 120 (FIG. 1), step 210 (FIG. 2), or step 310 (FIG. 3).

At step 415, a determination is made whether *Nannochloropsis* dominance in the algae cultivation system is being challenged by predators and/or invaders as described herein in connection with step 125 (FIG. 1), step 215 (FIG. 2), or step 315 (FIG. 3).

At step 420, if the level or amount of predators and/or invaders exceeds an actual or desired level, the salinity of the algae cultivation system may be adjusted to below that of seawater as described in connection with step 130 (FIG. 1) herein. At step 420, an effective amount of a disinfectant or an effective shock amount of a disinfectant may be applied to the algae cultivation system as described herein in connection with step 220 (FIG. 2) or step 225 (FIG. 2). Also at step 420, the temperature of the algae cultivation system may be adjusted to between approximately 21° C. and 32° C. The temperature may be controlled or adjusted in various growth systems by using the various means described herein.

If step 420 is performed, post-treatment observations may be made as described in connection with step 410. Generally, if the density or dominance of *Nannochloropsis* increases, one may assume the step(s) performed was effective (i.e. an effective protocol). If the density or dominance of *Nannochloropsis* decreases, one may assume the step(s) performed was ineffective (i.e. an ineffective protocol).

Various embodiments may include a system for maintaining dominance of *Nannochloropsis* in an algae cultivation system. The system may include a communications interface, a computer readable storage medium, a processor, and a salinity, disinfectant and/or temperature adjustment means. The computer readable storage medium may further comprise instructions for execution by the processor. The instructions for execution by the processor cause the processor to maintain dominance of the *Nannochloropsis* in the algae cultivation system. For example, the processor may execute the instructions on the computer readable medium to adjust a salinity in the algae cultivation system to approximately 0.5-10 PPT for a first predetermined period of time and to adjust the salinity in the algae cultivation system to approximately 20-45 PPT for a second predetermined period of time. The processor may execute other instructions described herein and remain within the scope of contemplated embodiments.

Another embodiment may include a computer readable storage medium having a computer readable code for operating a computer to perform a method of maintaining dominance of *Nannochloropsis* in an algae cultivation system. For example, the method may comprise the steps of applying an effective amount of a disinfectant to *Nannochloropsis* growing in the algae cultivation system, for adjusting a salinity in the algae cultivation system and/or for some or all of the other embodiments described herein.

Examples of computer readable storage medium may include discs, memory cards, servers and/or computer discs. Instructions may be retrieved and executed by a processor. Some examples of instructions include software, program code, and firmware. Instructions are generally operational when executed by the processor to direct the processor to operate in accord with embodiments of the invention. Although various modules may be configured to perform some or all of the various steps described herein, fewer or more modules may be provided and still fall within the scope of various embodiments.

EXAMPLES

Exemplary Laboratory Protocol for *Nannochloropsis* Culture

Algal cultivation: 800 ml cultures are maintained in one inch thick Roux flasks with continuous magnetic stirring. Continuous illumination at 700 MicroEinsteins per meter squared per second is provided by four 54-watt T5 fluorescent bulbs rated with a correlated color temperature of 5000K. 1% $CO_2$ is bubbled through scintered glass spargers at a rate sufficient to maintain a pH between 7.0 and 8.5. Photoautotrophic growth is maintained on UFM media formulated with artificial seawater (35 g/L Instant Ocean) containing 720 mg/L urea, 168 mg/L K2HPO4, 1.5 ml/L of a metals solution and 1 ml/L of a vitamin solution. The metals solution contains 39.7 g/L Fe(III)Cl3(6H2O), 30.0 g/L EDTA, 1.2 g/L MnCl2 (4H2O), 0.08 g/L CoCl2(6H2O), 0.16 g/L ZnSO4(7H2O), 0.067 g/L CuSO4(5H2O), 0.023 g/L Na2MoO4(2H2O). The vitamins solution contains 0.001 g/L vitamin B12, 0.001 g/L Biotin, and 0.2 g/L Thiamine. Cultures are diluted by exchanging 400 ml of culture with fresh media every day at the same time. From the 400 ml that are removed, the dry biomass concentration is determined as below.

Determination of culture biomass concentration: A sample of the culture between 0.5 and five milliliters is vacuum filtered through a pre-rinsed and pre-ashed Whatman GF/C glass microfiber filter disc. The cake is rinsed with twenty milliliters of 0.7M ammonium formate and dried for at least 2 hours at 105° C. The dried sample is weighed on an analytical balance and then ashed at 550° C. for at least 1 hour. The post ash weight is subtracted from the pre-ash weight and divided by the volume of the sample to get the ash-free dry biomass density in milligrams per milliliter.

Given the dilution volume and the previous day's dry biomass concentration, the current day's dry biomass concentration can be used to establish the culture's dry biomass productivity in grams per liter per day. This productivity value can then be compared across different experimental conditions.

For the hypochlorite kill curve, four cultures are measured for productivity as above, each of which receives a different dose of sodium hypochlorite with the fresh media that is added at dilution time. The final concentration of sodium hypochlorite following dilution for each of the four cultures is 0, 20, 40 and 80 milligrams per liter.

Achieving Salinities Less than or Greater than the Seawater Available

There are several basic methods for diluting algal cultivation reactors: batch mode, semi-continuously, or continuously.

In batch mode cultivation, the reactor is filled with a culture medium (liquid plus growth nutrients) and inoculated with an amount of algal suspension which may derived from an inoculum system or a previous batch. The liquid may be the seawater source available, or the seawater diluted with a water of lower salinity (freshwater or brackish water), or water that is higher in salinity than the seawater. The latter may be obtained by adding salts to the seawater or by first evaporating the seawater. At the end of the batch growth, substantially all of the contents of the reactor are removed for harvesting and processing of the algal biomass. The clarified harvest water may be recycled as the liquid for the next batch. If evaporation has occurred, the original salinity may be maintained by adding fresh water, or the salinity of the next batch may be greater if less or no fresh water is added. In the case of recycled effluents, successive batches may be allowed to get saltier until a desired salinity is reached.

In semi-continuous cultivation, a prescribed amount of culture medium is removed periodically (e.g., each day) and replaced with water. The replacement water may be new water or some combination of new water and clarified harvest water. The new water may be the seawater diluted with a water of lower salinity to obtain a salinity equal to or less than the seawater available. If the dilution water is the seawater that is available, any evaporative water losses may be replaced with fresh water to maintain salinity. Evaporative losses may be used to obtain a salinity which is higher than the seawater salinity without adding salts by not making up for evaporation, or not fully making up for evaporation. That is, the dilution water may be the seawater, or may be the seawater augmented with fresh water but not enough to make up for the evaporative loss. The removed culture medium may be clarified and recycled back to the reactor. Any salinity can be maintained, up to the solubility of the salts, by adjusting the amount of culture medium removed, and recycled with the available seawater used to make up for evaporative losses and for the harvest water that is not recycled. The salinity will increase in a step wise fashion until a steady state is achieved. The salinity of this steady state is determined by the ratio of water volume lost to evaporation to the volume of water not recycled (blow down water). Due to variation in rates of evaporation and in rainfall a steady state may not be attained, but the salinity of the cultivation medium can be kept within a prescribed range of values.

In continuous dilution, the culture medium is continuously removed and replaced with new water, which may be a combination of the seawater available with or without dilution with fresh water, or this plus recycled clarified harvest water. As in the previous cases of batch mode and semi-continuous dilution, salinities higher than the original seawater may be achieved by not making up for evaporative losses with fresh water or by recycling some or all of the clarified harvest waters. Again the salinity attained will depend on the ratio of evaporation volume to blow down water with the salinity of the reactor becoming equal to the available input water salinity times the quantity: one plus the ratio of evaporation volume to blow down volume.

Methods for Adding Chlorine Compounds to Algal Cultivation Reactors

Chlorine compounds may be added directly to the cultivation vessel. They may be added to the water of dilution of the cultivation vessel. In either case they may be added in solid (granular) form, liquid form, or as chlorine gas. In experiments performed by the inventors, the chlorine was added as a liquid (e.g., sodium hypochlorite). Typically, 10-12% solutions of sodium hypochlorite were diluted 10 to 100 fold and added directly to the cultivation reactor to achieve the initial concentration of sodium hypochlorite cited in each case.

Data on the Stability of *Nannochloropsis* Cultures as a Function of Salinity and Chlorine Additions In the following examples, *Nannochloropsis* was grown in outdoor, open, ponds in Vero Beach, Fla. The climate in Vero Beach is semitropical, with mild winters and hot, humid summers. It is a challenging climate for keeping outdoor algal cultures stable and productive. The overnight warmth encourages predation by protozoa, rotifers, and crustaceans. The humidity allows the airborne transport of competing algae, and thus increases the rate of invasion. In some of the examples the techniques applied were successful in keeping *Nannochloropsis* as the dominant alga, at ninety-five percent (95%) to nearly one-hundred percent (100%) of the algal biomass, even when competitors and/or predators were intentionally introduced to the algae cultivation system. In some cases, predators were undetectable most of the time, even after they were intentionally introduced.

Ten ponds (four 1.4 square meter, four 3 square meter, and two approximately 200 square meter) were used to test many conditions of salinity and chlorination over fifteen months. Not all of the conditions were run for that whole time period. The results from the following seven conditions are summarized below: 1) 35-36 PPT (full) seawater salinity, 2) 28-30 PPT (dilution of full seawater with fresh water in a ratio of 3:1), 3) 22-24 PPT (dilution of full seawater with fresh water in a ratio of about 2:1), 4) condition no. 3 with chlorine added to the pond every other day to an initial concentration of sodium hypochlorite of 3 ppm, 5) 10-12 PPT (dilution of full seawater with fresh water in a ratio of about 1:2), 6) 5-7 PPT (dilution of full seawater with fresh water in a ratio of about 1:6. and 7) about 1 PPT (dilution of seawater with fresh water in a ratio of about 1:40).

Condition one was run twice, once from Nov. 12, 2007 until the culture crashed around Dec. 12, 2007, about 30 days. It was run again from Apr. 16, 2008 until it crashed around May 26, 2008, about 40 days. At full salinity, the algae cultivation system was invaded by filaments of blue green algae and by various diatoms and other algae. Although *Nannochloropsis* was still dominant (e.g., 50% to 80%), the presence of the other organisms rendered the cultures less stable than those maintained at lower salinities. The percentages of the algae varied. Usually the other species caused clumping of themselves or of themselves with the *Nannochloropsis*. These clumps became invaded with amoeba and/or ciliated protozoa or were grazed by rotifers or crustaceans. Eventually, the cultures became unstable and much less productive.

Condition two was run in one 3 square meter pond from Feb. 3, 2008 until Jun. 12, 2008, about 130 days. It exhibited very low biomass densities on two occasions, almost crashing. Contamination levels were at 15-20% of the biomass (meaning that *Nannochloropsis* was 80-85% of the biomass) most of the time. Contamination was similar in nature to the full salinity condition. Clumping also occurred.

Condition three was run from Sep. 17, 2007 through Dec. 28, 2007, about 112 days without any stability problems. It was run again from Jan. 1, 2008 through Feb. 19, 2008, about 50 days without problem. *Nannochloropsis* was greater than 95% of the biomass most of the time, and greater than 90% all of the time. However, this condition was difficult to maintain over the summer months.

Condition four was run from Oct. 4, 2007 until Jun. 12, 2008, about 250 days without stability problems. Commercial chlorine solutions were added to the algae cultivation systems every other day to obtain an initial concentration of 2.5-3 mg of sodium hypochlorite. This concentration often had no effect on productivity when compared to condition three with no added chlorine. Cultures chlorinated in this way and grown at a salinity of 22-24 PPT had less contamination than non-chlorinated cultures at the same salinity during the warmer months of the year. During the cooler months there was no observable difference. The *Nannochloropsis* was cultivated without interruption and at greater than 95% dominance, throughout the entire cultivation period (over eight months). No predators were able to grow in these cultures, despite being added to the cultures along with competing algal species from other outdoor cultures. Species added included *Tetraselmis* and *Dunaliella*, along with amoeba, protozoa, and crustaceans. The *Tetraselmis* and *Dunaliella* cultures were decimated by the predators. The predators were not observable in the *Nannochloropsis* cultures after a few days.

However when this condition was run over the summer of 2008 in a 200 square meter pond in which temperatures reached 35 degrees C. often in the afternoon an increased frequency (sometimes every day) of addition of chlorine disinfectant was required to keep predator levels from increasing and biomass productivity was reduced compared to ponds at lower temperature and/or lower salinity The surfaces of this pond fouled within one week, and significant sedimentation of organic material (bacterial, algal, and zooplankton) occurred within three weeks.

Outdoor culture temperature may be controlled by the amount of water per unit area of pond, e.g., by changing the depth. At 20 cm depth, the culture may increase to 40° C. during the afternoon in humid climates. This temperature may be lowered to approximately 35 degrees Celsius by increasing the depth to 30 cm. Temperature management with culture depth, combined with the above methods for maintaining the dominance of *Nannochloropsis* allows optimal production in outdoor, open cultures.

Condition five was run for almost five months in 2007-2008. *Nannochloropsis* was maintained nearly unialgal in culture, and/or as the dominant organism (e.g., >95%).

Condition six was run from Aug. 23, 2008 until Dec. 1, 2008, about 100 days without stability problems in a 3 square meter pond and in a 200 square meter pond. *Nannochloropsis* was over 99% of the biomass all of the time even though pond temperatures equaled or exceeded 35 degrees C. many afternoons in August and September. Predators were not observed. There was no fouling in the pond, nor any sedimentation of organic material on the bottom of the pond.

Condition seven was run from Nov. 24, 2008-Dec. 4, 2008 without stability problems. *Nannochloropsis* was over 99% of the biomass all of the time. However, biomass productivity was reduced (see Table above).

All of the cultures had lowered biomass densities for explainable reasons such as cold weather, rainy or cloudy weather, or operator errors. By "crash" it is meant that the culture density of *Nannochloropsis* became so low that the pond had to be cleaned and started from another pond. In summary, several trends were observed over 15 months of cultivation of *Nannochloropsis*. Temperatures at and above 30° C. resulted in the dominance of *Nannochloropsis* being challenged by invading species and predators. Chlorine addition became more frequent and required higher doses as temperatures climbed above 30° C. The lower the salinity, and especially at salinities below 7 PPT, the easier it became to maintain the dominance of *Nannochloropsis*, even at temperatures above 35° C. At these lower salinities, the ponds surfaces remained clean and little or no accumulation of sediment occurred on the pond bottom. There was almost no dependence of the lipid content or lipid composition on temperature or salinity below 35 PPT.

While various embodiments are described herein, it should be understood that they are presented by way of example only, and not limitation. Thus, the breadth and scope of a preferred embodiment should not be limited by any of the described exemplary embodiments.

What is claimed is:

1. A method for maintaining dominance of *Nannochloropsis* in an algae cultivation system and for maximizing biomass production by the *Nannochloropsis* in the algae cultivation system, the method comprising:
   inoculating the algae cultivation system with a culture of *Nannochloropsis*;
   administering an effective amount of sodium hypochlorite to the algae cultivation system having the *Nannochloropsis*, the effective amount of sodium hypochlorite resulting in an approximate initial concentration of between 20 milligrams/liter and 40 milligrams/liter of sodium hypochlorite in the algae cultivation system having the *Nannochloropsis*; and
   maintaining the sodium hypochlorite concentration of the algae cultivation system having the *Nannochloropsis* at a concentration of between 20 milligrams/liter and 40 milligrams/liter on a daily basis.

2. The method of claim 1, the method further comprising: visually observing the algae cultivation system for a presence of a predator or a competing algae species.

3. The method of claim 2, the method further comprising: re-administering the effective amount of sodium hypochlorite if the presence of the predator or the competing algae species appears to challenge the dominance of *Nannochloropsis* growing in the algae cultivation system.

4. The method of claim 1, further comprising:
adding a shock amount of sodium hypochlorite that results in an approximate concentration of between 40 milligrams/liter and 80 milligrams/liter of sodium hypochlorite in the algae cultivation system before the maintaining step.

5. The method of claim 1, further comprising: adjusting a salinity in the algae cultivation system to between approximately 0.5 PPT and 28 PPT.

6. The method of claim 5, the method further comprising:
adjusting a temperature within the algae cultivation system to between approximately 21° C. and 32° C.

7. The method of claim 6, further comprising:
adding a shock amount of sodium hypochlorite that results in an approximate concentration of between 40 milligrams/liter and 80 milligrams/liter of sodium hypochlorite in the algae cultivation system before the maintaining step.

8. The method of claim 1, further comprising: adjusting a salinity in the algae cultivation system to below that of seawater for a first predetermined period of time; and increasing the salinity in the algae cultivation system while maintaining the salinity below 45 PPT for a second predetermined period of time.

9. The method of claim 8, further comprising:
adding a shock amount of sodium hypochlorite that results in an approximate concentration of between 40 milligrams/liter and 80 milligrams/liter of sodium hypochlorite in the algae cultivation system before the maintaining step.

10. The method of claim 8, the method further comprising:
adjusting a temperature within the algae cultivation system to between approximately 21° C. and 32° C.

11. The method of claim 8, wherein the algae cultivation system includes seawater.

12. The method of claim 8, wherein the adjusting is performed with fresh water.

13. The method of claim 8, wherein the adjusting or increasing is performed with a mixture of seawater and fresh water.

14. The method of claim 8, wherein the algae cultivation system is in a photobioreactor.

15. The method of claim 8, wherein the algae cultivation system is in an open pond.

16. The method of claim 8, wherein the algae cultivation system is in an open vessel.

17. The method of claim 8, wherein the algae cultivation system is in a closed vessel.

18. A method for maintaining dominance of *Nannochloropsis* in an algae cultivation system, the method comprising:
inoculating the algae cultivation system with a culture of *Nannochloropsis*;
administering an effective amount of sodium hypochlorite to the algae cultivation system having the *Nannochloropsis*, the effective amount of sodium hypochlorite resulting in an approximate initial concentration of between 20 milligrams/liter and 40 milligrams/liter of sodium hypochlorite in the algae cultivation system having the *Nannochloropsis*; and
maintaining the sodium hypochlorite concentration of the algae cultivation system having the *Nannochloropsis* at a concentration of between 20 milligrams/liter and 40 milligrams/liter on a daily basis.

19. The method of claim 5, further comprising:
adjusting the salinity in the algae cultivation system having the *Nannochloropsis* to approximately 17.5 PPT.

20. The method of claim 18, further comprising: adjusting a salinity in the algae cultivation system having a *Nannochloropsis* culture to below approximately 10 PPT for a first predetermined period of time; and increasing the salinity in the algae cultivation system having the *Nannochloropsis* culture to above approximately 37 PPT for a second predetermined period of time.

21. The method of claim 1, further comprising:
adjusting a salinity in the algae cultivation system having the *Nannochloropsis* to approximately 17.5 PPT.

* * * * *